| (12) | United States Patent | (10) Patent No.: | US 8,709,060 B2 |
|---|---|---|---|
| | Osborne | (45) Date of Patent: | Apr. 29, 2014 |

(54) PROSTHESIS DEPLOYMENT SYSTEM

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1181 days.

(21) Appl. No.: 12/158,400

(22) PCT Filed: Dec. 22, 2006

(86) PCT No.: PCT/US2006/049240
§ 371 (c)(1),
(2), (4) Date: Oct. 17, 2008

(87) PCT Pub. No.: WO2007/076114
PCT Pub. Date: Jul. 5, 2007

(65) Prior Publication Data
US 2011/0054585 A1    Mar. 3, 2011

Related U.S. Application Data

(60) Provisional application No. 60/753,502, filed on Dec. 23, 2005.

(51) Int. Cl.
*A61F 2/06* (2013.01)

(52) U.S. Cl.
USPC ........................................................ 623/1.11

(58) Field of Classification Search
USPC ......................... 623/1.11, 1.12, 1.23; 606/194
See application file for complete search history.

(56) References Cited

U.S. PATENT DOCUMENTS

| 3,502,527 A | 3/1970 | Borden |
|---|---|---|
| 4,362,150 A | 12/1982 | Lombardi et al. |

(Continued)

FOREIGN PATENT DOCUMENTS

| EP | 0 696 447 A2 | 2/1996 |
|---|---|---|
| EP | 1 374 943 A1 | 1/2004 |

(Continued)

OTHER PUBLICATIONS

International Preliminary Report on Patentability dated Jul. 8, 2008 for International Application No. PCT/US2006/049240.

(Continued)

*Primary Examiner* — Darwin Erezo
*Assistant Examiner* — Amy Shipley
(74) *Attorney, Agent, or Firm* — Brinks Gilson & Lione

(57) ABSTRACT

A trigger wire release mechanism is disclosed that includes a control member for selectively releasing a trigger wire (22, 44) from a prosthesis retaining device. The control member includes an elongate body member (36) and a guide member (24, 25, 93, 94) slidably disposed on the elongate body member. The trigger wire 1 (22, 44) includes a distal end coupled to the prosthesis retaining device and a proximal end coupled to the guide member. The guide member (24, 25, 93, 94) can be moved from a distal end of the elongate body (36) to a proximal end of the elongate body, thereby disengaging the trigger wire (22, 44) from the retaining device. The control member may include a locking mechanism (120) for limiting the axial position of the guide member (24, 25, 93, 94) along the elongate body member (36). A prosthesis control member (81) is also disclosed. The prosthesis control member (81) is adapted to control the position of the prosthesis during deployment.

14 Claims, 11 Drawing Sheets

(56) References Cited

U.S. PATENT DOCUMENTS

| | | |
|---|---|---|
| 4,512,351 A | 4/1985 | Pohndorf |
| 4,562,596 A | 1/1986 | Kornberg |
| 4,569,347 A | 2/1986 | Frisbie |
| 4,665,918 A | 5/1987 | Garza et al. |
| 4,690,175 A | 9/1987 | Ouchi et al. |
| 4,762,129 A | 8/1988 | Bonzel |
| 4,921,484 A | 5/1990 | Hillstead |
| 4,960,410 A | 10/1990 | Pinchuk |
| 5,078,720 A | 1/1992 | Burton et al. |
| 5,092,877 A | 3/1992 | Pinchuk |
| 5,158,553 A | 10/1992 | Berry et al. |
| 5,201,757 A | 4/1993 | Heyn et al. |
| 5,221,270 A | 6/1993 | Parker |
| 5,275,622 A | 1/1994 | Lazarus et al. |
| 5,380,304 A | 1/1995 | Parker |
| 5,415,664 A | 5/1995 | Pinchuk |
| 5,425,711 A | 6/1995 | Ressemann et al. |
| 5,445,646 A * | 8/1995 | Euteneuer et al. ............ 606/198 |
| 5,507,768 A | 4/1996 | Lau et al. |
| 5,534,007 A | 7/1996 | St. Germain et al. |
| 5,562,728 A | 10/1996 | Lazarus et al. |
| 5,599,305 A | 2/1997 | Hermann et al. |
| 5,626,603 A | 5/1997 | Venturelli et al. |
| 5,669,936 A | 9/1997 | Lazarus |
| 5,683,451 A | 11/1997 | Lenker et al. |
| 5,690,644 A | 11/1997 | Yurek et al. |
| 5,695,517 A * | 12/1997 | Marin et al. ................. 623/1.13 |
| 5,700,253 A | 12/1997 | Parker |
| 5,720,776 A | 2/1998 | Chuter et al. |
| 5,728,067 A | 3/1998 | Enger |
| 5,749,357 A | 5/1998 | Linder |
| 5,817,101 A | 10/1998 | Fiedler |
| 6,048,338 A | 4/2000 | Larson et al. |
| 6,056,759 A | 5/2000 | Fiedler |
| 6,113,608 A | 9/2000 | Monroe et al. |
| 6,206,888 B1 | 3/2001 | Bicek et al. |
| 6,206,931 B1 | 3/2001 | Cook et al. |
| 6,254,611 B1 | 7/2001 | Vrba |
| 6,287,315 B1 | 9/2001 | Wijeratne et al. |
| 6,306,124 B1 | 10/2001 | Jones et al. |
| 6,319,267 B1 | 11/2001 | Kurz |
| 6,346,092 B1 | 2/2002 | Leschinsky |
| 6,368,344 B1 | 4/2002 | Fitz |
| 6,402,760 B1 | 6/2002 | Fedida |
| 6,475,209 B1 | 11/2002 | Larson et al. |
| 6,514,261 B1 | 2/2003 | Randall et al. |
| 6,579,297 B2 | 6/2003 | Bicek et al. |
| 6,589,227 B2 | 7/2003 | Sønderskov Klint |
| 6,605,109 B2 | 8/2003 | Fiedler |
| 6,626,934 B2 | 9/2003 | Blaeser et al. |
| 6,648,854 B1 | 11/2003 | Patterson et al. |
| 6,648,857 B1 | 11/2003 | Pedigo |
| 6,669,716 B1 | 12/2003 | Gilson et al. |
| 6,746,478 B2 | 6/2004 | Jayaraman |
| 6,849,084 B2 | 2/2005 | Rabkin et al. |
| 6,858,034 B1 | 2/2005 | Hijlkema et al. |
| 6,881,201 B1 | 4/2005 | Duchamp |
| 6,911,039 B2 | 6/2005 | Shiu et al. |
| 7,122,050 B2 | 10/2006 | Randall et al. |
| 7,335,224 B2 * | 2/2008 | Ohlenschlaeger ............ 623/1.11 |
| 7,435,253 B1 * | 10/2008 | Hartley et al. ............... 623/1.12 |
| 7,803,177 B2 * | 9/2010 | Hartley et al. ............... 623/1.11 |
| 8,043,354 B2 * | 10/2011 | Greenberg et al. .......... 623/1.12 |
| 8,262,718 B2 * | 9/2012 | Chuter et al. ................ 623/1.11 |
| 8,333,797 B2 * | 12/2012 | Goodson et al. ............. 623/1.11 |
| 8,500,792 B2 * | 8/2013 | Berra ........................... 623/1.12 |
| 2001/0012944 A1 | 8/2001 | Bicek et al. |
| 2001/0034514 A1 | 10/2001 | Parker |
| 2001/0049547 A1 | 12/2001 | Moore |
| 2002/0045929 A1 | 4/2002 | Diaz |
| 2002/0183827 A1 | 12/2002 | Derus et al. |
| 2003/0055401 A1 | 3/2003 | Larson et al. |
| 2003/0105427 A1 | 6/2003 | Lee et al. |
| 2003/0109886 A1 | 6/2003 | Keegan et al. |
| 2003/0233140 A1 | 12/2003 | Hartley et al. |
| 2004/0010265 A1 | 1/2004 | Karpiel |
| 2004/0054396 A1 | 3/2004 | Hartley et al. |
| 2004/0098079 A1 * | 5/2004 | Hartley et al. ............... 623/1.11 |
| 2004/0106974 A1 | 6/2004 | Greenberg et al. |
| 2004/0127912 A1 | 7/2004 | Rabkin et al. |
| 2004/0133158 A1 | 7/2004 | Keith et al. |
| 2004/0133264 A1 | 7/2004 | Moore |
| 2004/0230286 A1 | 11/2004 | Moore et al. |
| 2005/0060018 A1 | 3/2005 | Dittman |
| 2005/0085890 A1 | 4/2005 | Rasmussen et al. |
| 2005/0090887 A1 | 4/2005 | Pryor |
| 2005/0107862 A1 | 5/2005 | Ohlenschlaeger |
| 2005/0149159 A1 | 7/2005 | Andreas et al. |
| 2005/0171479 A1 | 8/2005 | Hruska et al. |
| 2005/0182476 A1 | 8/2005 | Hartley et al. |
| 2005/0273151 A1 | 12/2005 | Fulkerson et al. |
| 2005/0283221 A1 | 12/2005 | Mann et al. |
| 2005/0288628 A1 | 12/2005 | Jordan et al. |
| 2006/0004433 A1 * | 1/2006 | Greenberg et al. .......... 623/1.11 |
| 2006/0058864 A1 * | 3/2006 | Schaeffer et al. ............ 623/1.11 |
| 2006/0224112 A1 | 10/2006 | Lentz |
| 2007/0060999 A1 | 3/2007 | Randall et al. |
| 2007/0293934 A1 * | 12/2007 | Grewe ......................... 623/1.12 |
| 2009/0024137 A1 * | 1/2009 | Chuter et al. ................ 606/108 |
| 2009/0149938 A1 * | 6/2009 | Grewe et al. ................ 623/1.11 |
| 2010/0168838 A1 * | 7/2010 | Hartley et al. ............... 623/1.11 |
| 2010/0198328 A1 * | 8/2010 | Hartley et al. ............... 623/1.11 |
| 2011/0054585 A1 * | 3/2011 | Osborne ...................... 623/1.11 |
| 2011/0144735 A1 * | 6/2011 | Hartley et al. ............... 623/1.11 |
| 2012/0010696 A1 * | 1/2012 | Greenberg et al. .......... 623/1.12 |

FOREIGN PATENT DOCUMENTS

| | | |
|---|---|---|
| EP | 1 637 176 A1 | 3/2006 |
| EP | 1 810 644 A2 | 7/2007 |
| WO | WO 95/11055 A1 | 4/1995 |
| WO | WO 98/53761 A1 | 12/1998 |
| WO | WO 99/29262 A1 | 6/1999 |
| WO | WO 03/005936 A2 | 1/2003 |
| WO | WO 03/034948 A1 | 5/2003 |
| WO | WO 03/053287 A1 | 7/2003 |
| WO | WO 03/101347 A1 | 12/2003 |
| WO | WO 2004/028399 A2 | 4/2004 |
| WO | WO 2004/060442 A2 | 7/2004 |
| WO | WO 2005/037142 A2 | 4/2005 |
| WO | WO 2005/099629 A1 | 10/2005 |
| WO | WO 2007/076114 A2 | 7/2007 |

OTHER PUBLICATIONS

International Search Report dated Oct. 9, 2007 for International Application No. PCT/US2006/049240.

* cited by examiner

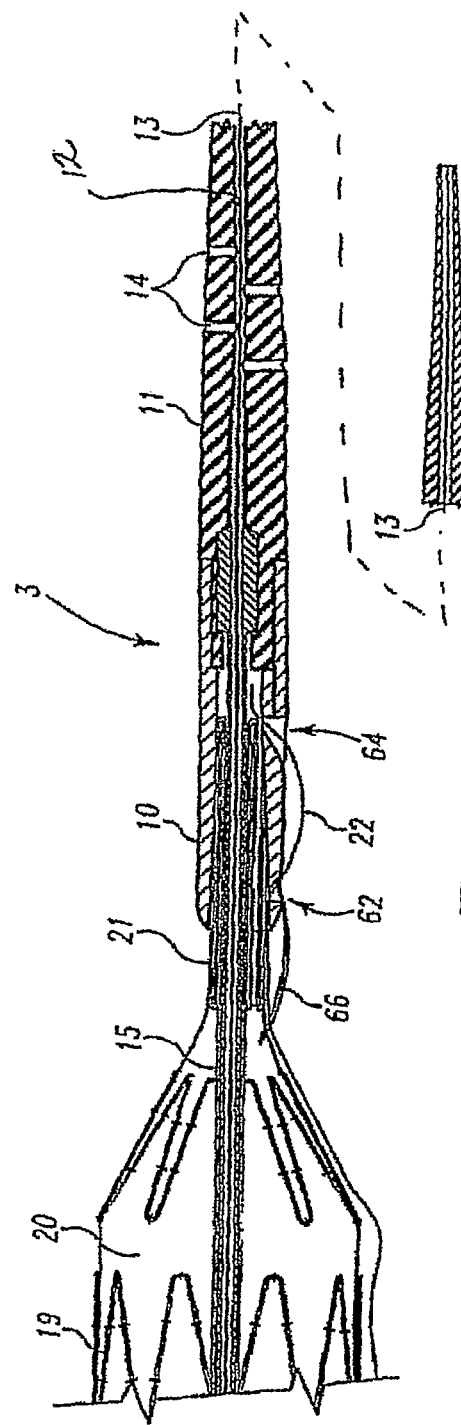

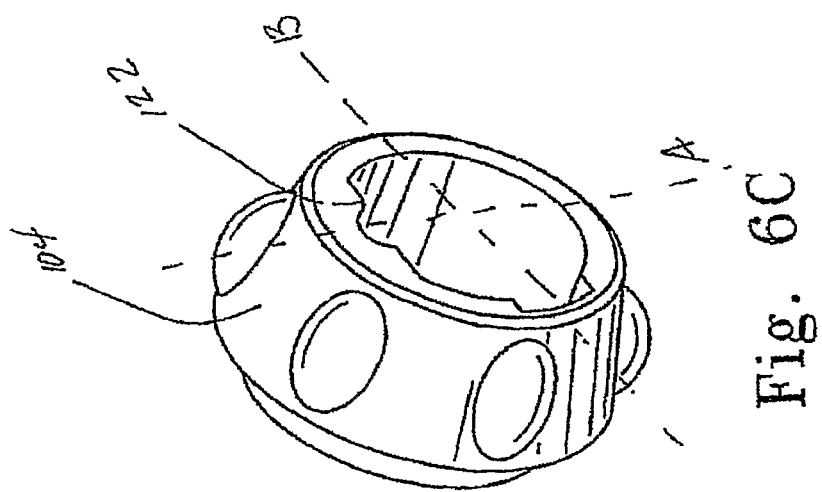
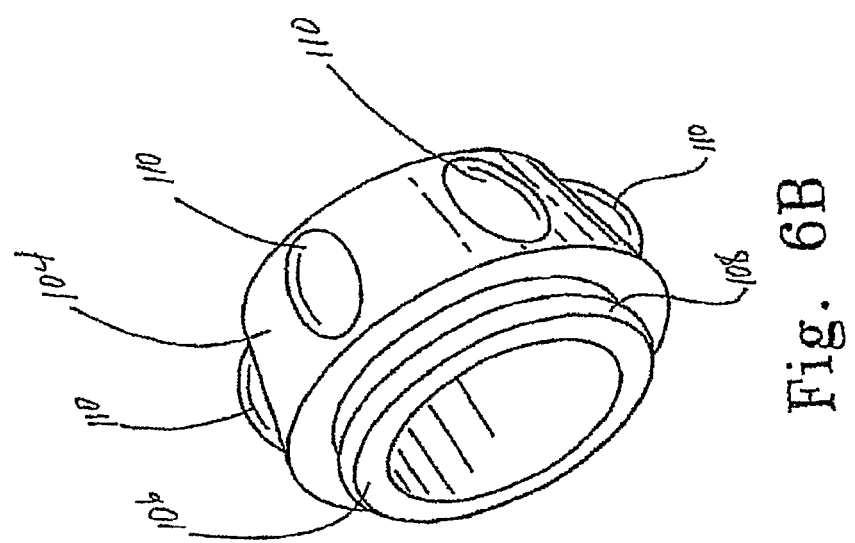
Fig. 6B
Fig. 6C

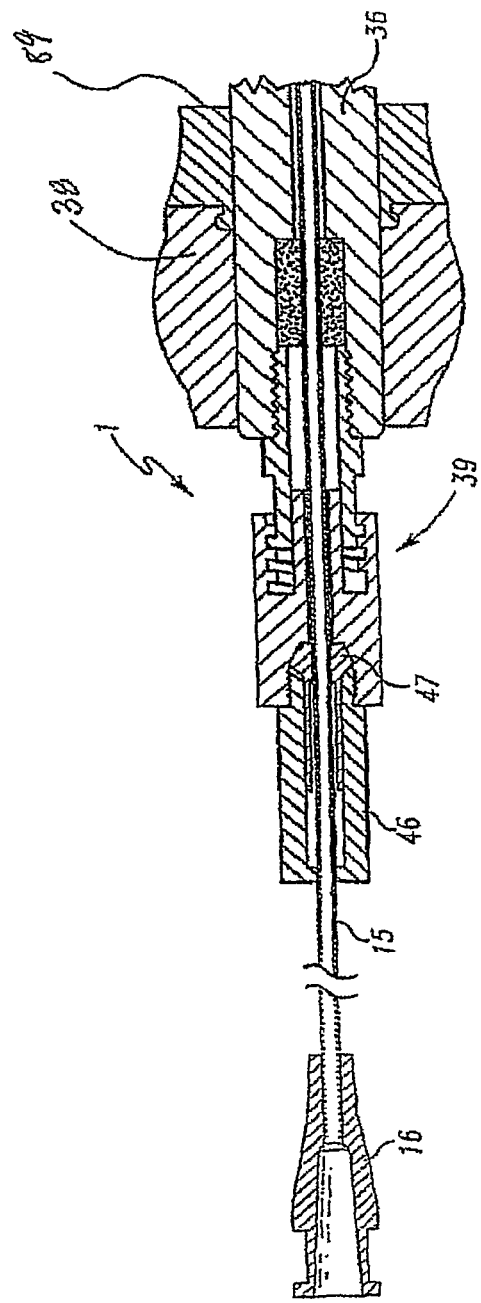

PROSTHESIS DEPLOYMENT SYSTEM

CROSS-REFERENCE TO RELATED APPLICATIONS

This application is a nationalization of PCT application PCT/US2006/049240 filed on Dec. 22, 2006. This application claims the benefit of the filing date under 35 U.S.C. §119(e) of U.S. Provisional Patent Application Ser. No. 60/753,502, filed Dec. 23, 2005, which is hereby incorporated by reference.

TECHNICAL FIELD

This invention relates to a medical device and, in particular an introducer and a means for retaining and releasing an expandable, intraluminal prosthesis for the endovascular repair of diseased or damaged vessels.

Throughout this specification the terms distal and distally are used for a position or direction towards the patient's heart and the terms proximal and proximally are used for a position or direction away from the patient's heart.

BACKGROUND OF THE INVENTION

The deployment of intraluminal prostheses into the lumen of a patient from a remote location by the use of a deployment device or introducer has been disclosed in a number of patents and patent applications. For example, U.S. Pat. No. 4,562,596 entitled "Aortic Graft, Device and Method for Performing an Intraluminal Abdominal Aortic Aneurysm Repair", which is herein incorporated by reference, proposes the retention of a self expanding graft within a sleeve until it is to be deployed, at which time the sleeve is withdrawn and the graft is allowed to expand. U.S. Pat. No. 4,665,918 entitled "Prosthesis System and Method", which is herein incorporated by reference, proposes a system and method for the deployment of a prosthesis in a blood vessel. The prosthesis is positioned between a delivery catheter and an outer sheath and expands outwardly upon removal of the sheath.

United States Published Patent Application No. 20050060018 entitled "Prosthesis Deployment System," which is herein incorporated by reference, discloses an introducer for an expandable endovascular prosthesis. A self-expanding prosthesis is radially disposed within a distal portion of an outer sheath. A dilator or positioner is radially disposed within a proximal portion of the outer sheath so that the dilator distal end engages the prosthesis proximal end. To deploy the prosthesis, the operator withdraws the outer sheath over the dilator portion and the prosthesis while holding the dilator portion steady, thereby exposing the prosthesis and allowing the prosthesis to expand radially outwardly. In practice, the outer sheath fits tightly over the dilator. Because of the tight fit, withdrawal of the sheath can be difficult, requiring a very tight grip on the dilator by the operator. However, the dilator has a relatively small diameter and does not provide an adequate gripping surface. There is a need in the art for an improved prosthesis deployment system that addresses this issue.

The outer sheath of a prosthesis deployment system should be flexible and capable of conforming to highly tortuous body lumen systems without deforming or kinking. The outer sheath should also be strong and capable of maintaining its shape during delivery. U.S. Pat. No. 5,380,304 entitled "Flexible, Kink-Resistant, Introducer Sheath and Method of Manufacture," which is herein incorporated by reference, discloses an apparatus and method of manufacturing an introducer sheath for percutaneous vascular access. United States Published Patent Application No. 20010034514 entitled "Introducer Sheath," which is herein incorporated by reference, discloses an improved introducer sheath apparatus. There is a need in the art for an improved prosthesis deployment system that addresses this issue.

Today, many endoluminal prostheses are radially self-expanding. Radially self-expanding prostheses are advantageous because they do not require complicated and bulky balloon catheter systems for deployment. Such prostheses present a challenge, however, in that once a prosthesis end is released and anchored into the body lumen, subsequent positioning can be difficult. This is particularly the case if the ends of the prosthesis include anchoring mechanisms to secure the prosthesis to the body lumen. As a consequence, many deployment devices have been proposed that allow the self-expanding prosthesis to be partially expanded while providing a mechanism for retaining the prosthesis ends until the prosthesis has been properly positioned.

For example, in United States Published Patent Application No. 20050060018, discussed above, the introducer comprises a retention section for retaining a proximal end of the prosthesis thereto. The proximal end of the prosthesis is retained by a trigger wire. The trigger wire can be removed from the introducer to release the proximal end of the prosthesis into the body lumen. The deployment system disclosed in United States Published Patent Application No. 20050060018 has various advantages over other delivery systems including that it provides the operator with greater control over the prosthesis during deployment before the proximal prosthesis end is released into the body lumen. However, it can be inconvenient and awkward for the operator to have to remove and store the trigger wire during a procedure. There is a need in the art for a prosthesis deployment system that has a trigger wire mechanism for retaining a prosthesis end, wherein the prosthesis end can be deployed without having to remove the trigger wire.

United States Published Patent Application No. 20050085890 entitled "Prosthesis Deployment System Retention Device," which is herein incorporated by reference, discloses another introducer for an expandable endovascular prosthesis. The introducer comprises a retention section for retaining a proximal end of the prosthesis thereto, similar to that of United States Published Patent Application No. 20050060018. The introducer comprises an additional retention section for retaining a distal end of the prosthesis thereto. The prosthesis is retained in the distal retention section by a second trigger wire. The second trigger wire is removed from the introducer to release the distal end of the prosthesis into the body lumen. The invention disclosed in United States Published Patent Application No. 20050085890 has many of the same advantages and challenges of United States Published Patent Application No. 20050060018; described above.

PCT Patent Publication Number No. WO98/53761 entitled "A Prosthesis and a Method and Means of Deploying a Prosthesis," United States Published Patent Application No. 20030233140 entitled "Trigger Wire System," and United States Published Patent Application No. 20040098079 entitled "Thoracic Aortic Stent Graft Deployment Device" each disclose introducer devices having trigger wires that are adapted for retaining a portion of a prosthesis during deployment. The disclosures of PCT Patent Publication No. WO98/53761, United States Published Patent Application No. 20030233140, and United States Published Patent Application No. 20040098079 are herein incorporated by reference.

Many prosthesis delivery systems have haemostatic valve assemblies for controlling blood loss through the system during the procedure. Valve assemblies are disposed on the introducer and are adapted to provide a radial seal about various interventional devices used during the procedure. Valve sealing assemblies may comprise disk type automatic or self closing valves. Disk type valves have various advantages including that they are relatively inexpensive and they provide an adequate seal around a variety of interventional devices having a range of diameters. However, no single disk valve is capable of sealing over the entire range of interventional device diameters, for example between 0.089 cm (0.035 inches) and 0.635 cm (0.250 inches. United States Published Patent Application No 20050171479 entitled "Hemostatic Valve Assembly", which is herein incorporated by reference, discloses an iris-type valve assembly for controlling a flow of liquid. There is a need in the art for a prosthesis deployment system having an improved haemostatic valve assembly that addresses this issue.

Finally, various published patent applications and patents disclose features that relate to various aspects of prosthesis deployment systems. These include, but are not limited to:

a. United States Published Patent Application No. 20040054396 entitled "Stent-Graft Fastening," which is herein incorporated by reference, discloses arrangements for fastening stents onto grafts particularly for exposed stents.

b. PCT Patent Publication Number No. WO03/053287 entitled "Stent Graft with Improved, Graft Adhesion," which is herein incorporated by reference, discloses arrangements on stent grafts for enhancing the adhesion of such stent grafts into walls of vessels in which they are deployed.

c. U.S. Pat. No. 5,720,776 entitled "Expandable Transluminal Graft Prosthesis for Repair of Aneurysm," which is herein incorporated by reference, discloses improved barbs with various forms of mechanical attachment to a stent.

d. U.S. Pat. No. 6,206,931 entitled "Graft Prosthesis Materials," which is herein incorporated by reference, discloses graft prosthesis materials and a method for implanting, transplanting replacing and repairing a part of a patient and particularly the manufacture and use of a purified, collagen based matrix structure removed from a submucosa tissue source.

e. PCT Patent Publication Number No. WO99/29262 entitled "Endoluminal Aortic Stents,", which is herein incorporated by reference, discloses a fenestrated prosthesis for placement where there are intersecting arteries.

f. PCT Patent Publication Number No. WO03/034948 entitled "Prostheses for Curved Lumens," which is herein incorporated by reference, discloses prostheses with arrangements for bending the prosthesis for placement into curved lumens.

SUMMARY OF THE INVENTION

In accordance with a first aspect of the invention, there is provided a trigger wire release mechanism for releasing a retained end of a prosthesis, the trigger wire release mechanism comprising: a prosthesis retaining device arranged to engage an end of the prosthesis; a trigger wire having a distal end and a proximal end, the distal end being arranged to selectively couple the prosthesis retaining device to the prosthesis; a control mechanism comprising an elongate body member and a guide member, the elongate body member having a proximal end and a distal end, an exterior surface, and an interior surface, the interior surface defining a chamber extending longitudinally with the elongate body member; wherein the trigger wire proximal end is operably coupled to the guide member in the chamber and the guide member is slidably disposed between a generally distal position and a generally proximal position along the elongate body member to selectively disengage the prosthesis retaining device from the prosthesis. The trigger wire release mechanism may comprise a locking mechanism to selectively limit axial displacement of the guide member on the elongate body member. The trigger wire release mechanism may comprise a stop disposed on the distal end of the elongate body member to retain the guide member on the elongate body member. The trigger wire release mechanism may comprise first and second trigger wires attached to respective first and second prosthesis retaining devices located at opposite ends of the prosthesis.

In accordance with a second aspect of the invention, there is provided an introducer for a prosthesis, the introducer comprising a trigger wire release mechanism according to the first aspect.

In accordance with a third aspect of the invention, there is provided an introducer for a prosthesis, the introducer comprising: an elongate pusher having a distal end in communication with a proximal end of the prosthesis; a flexible sheath slidably disposed over the elongate pusher, the flexible sheath releasably covering the prosthesis in a compressed state, wherein the prosthesis is arranged to be released by withdrawing the flexible sheath proximally over the elongate pusher while controlling the position of the prosthesis; and a control member disposed on a proximal portion of the elongate pusher capable of transferring a force between an operator and the elongate pusher for controlling the position of the prosthesis while the sheath is withdrawn from the prosthesis.

The control member may comprise a generally deformable tubular body disposed about the elongate pusher. The control member is capable of transferring force between an operator and the elongate pusher. The control member may be slidably disposed along the elongate pusher.

In another aspect of the invention, the introducer may comprise a haemostatic valve assembly for controlling blood loss during a procedure. The haemostatic valve assembly is radially disposed about a proximal end of the flexible sheath. The haemostatic valve assembly includes a disc valve and an iris-type valve.

In another aspect of the invention, the introducer may comprise a flexible sheath that releasably covers the prosthesis in a compressed state and an elongate pusher disposed within the flexible sheath and having a distal end in communication with a proximal end of the prosthesis. A distal portion of the flexible sheath may comprise a kink-resistant sandwich construction including an elongate inner tube having a passageway extending longitudinally therethrough, a coil having a plurality of longitudinally-positioned turns defining a plurality of spaces therebetween, and an elongate outer tube disposed longitudinally around the coil and the inner tube. The inner tube and the outer tube are connected through the spaces between the coil turns.

BRIEF DESCRIPTION OF THE DRAWING

FIG. 3 is a sectional detail view of a portion of the introducer illustrating the distal end of the prosthesis.

FIG. 6B is perspective view of a portion of a trigger wire knob.

FIG. 6C is another perspective view of a portion of a trigger wire knob.

FIG. 7 is a sectional view of a portion of the introducer illustrating the pin vise clamp and the medical reagent introduction tube.

DETAILED DESCRIPTION

Figure 1:
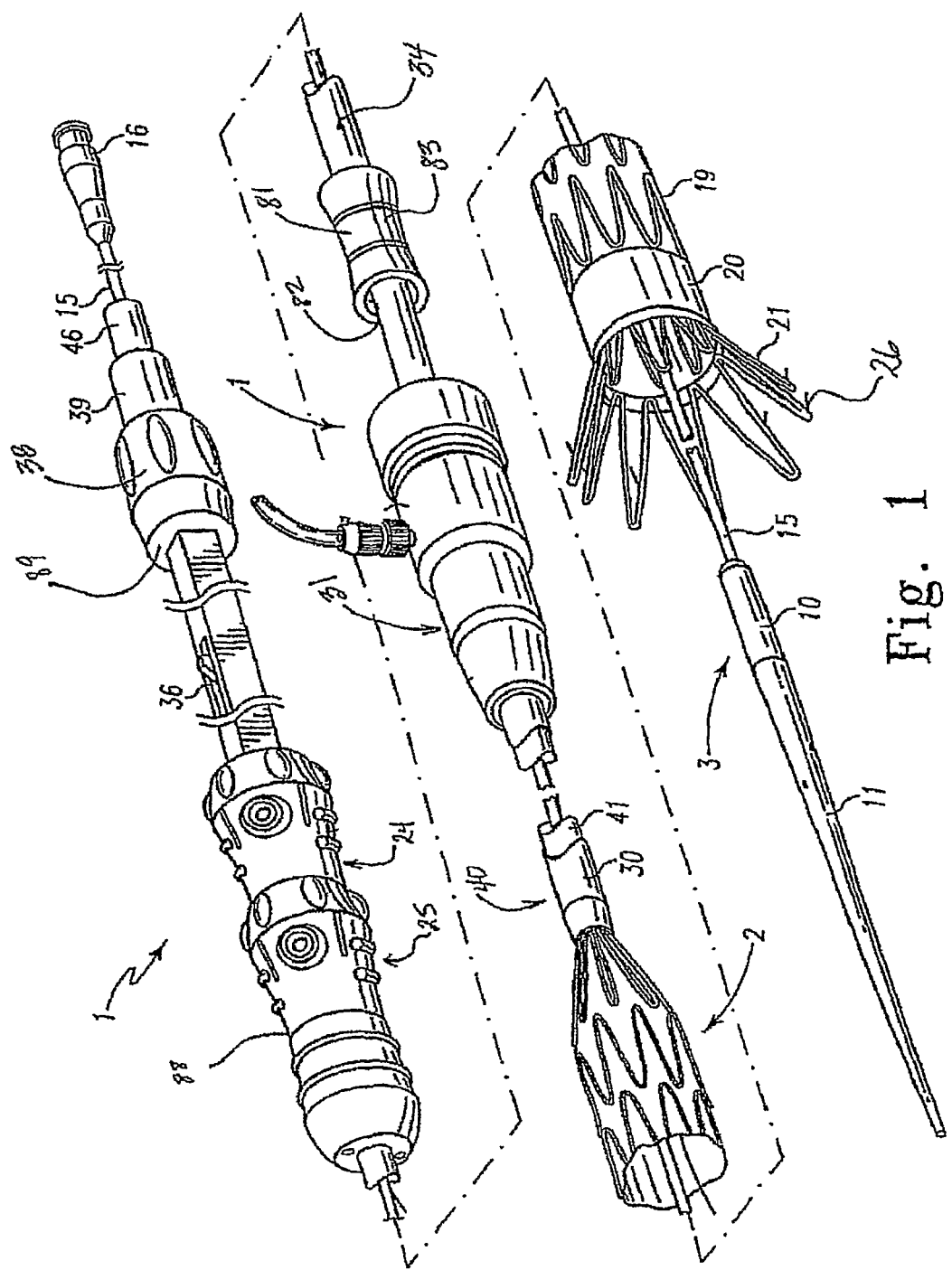
FIG. 1 is a perspective view of selected segments of an introducer of the present invention with a prosthesis partially deployed.

FIG. 1 shows an endovascular deployment system, also known as an introducer, for deploying a prosthesis 20 in a lumen of a patient during a medical procedure. The introducer includes an external manipulation section 1, a proximal positioning mechanism or attachment region 2, and a distal positioning mechanism or attachment region 3. During a medical procedure to deploy the prosthesis 20, the proximal and distal attachment regions 2 and 3 will travel through the lumen to a desired deployment site. The external manipulation section 1, which is acted upon by a user to manipulate the introducer, remains outside of the patient throughout the procedure.

Figure 2:
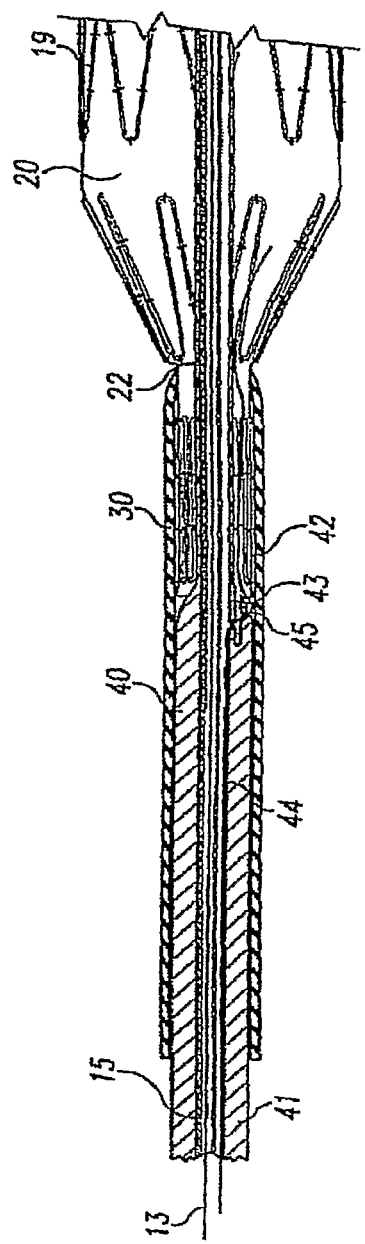
FIG. 2 is a sectional detail view of a portion of the introducer illustrating the proximal end of the prosthesis.

The prosthesis 20 can comprise a tubular graft material, such as Dacron, with self-expanding stents 19 attached thereto as shown in FIGS. 2 and 3. The self-expanding stents 19 cause the prosthesis 20 to expand during its release from the introducer. The prosthesis 20 also includes an exposed self-expanding zigzag stent 21, which is a bare wire stent having barbs 26 that extend from the stent distal end. When the self-expanding stent 21 is released, the barbs 26 anchor the distal end of the prosthesis 20 to the surrounding lumen (not shown).

The prosthesis 20 is retained in a compressed condition by a sheath 30. The sheath 30 radially compresses the prosthesis 20 over a distal portion of a thin walled tube 15. The thin walled tube 15 is generally flexible and may comprise metal. A tube 41, which can be made of plastic, is coaxial with and radially outside the thin tube 15. The distal end of the tube 41 is adjacent the proximal end of the prosthesis 20. The tube 41 acts as a pusher to release the prosthesis 20 from the introducer during delivery.

Figure 5:
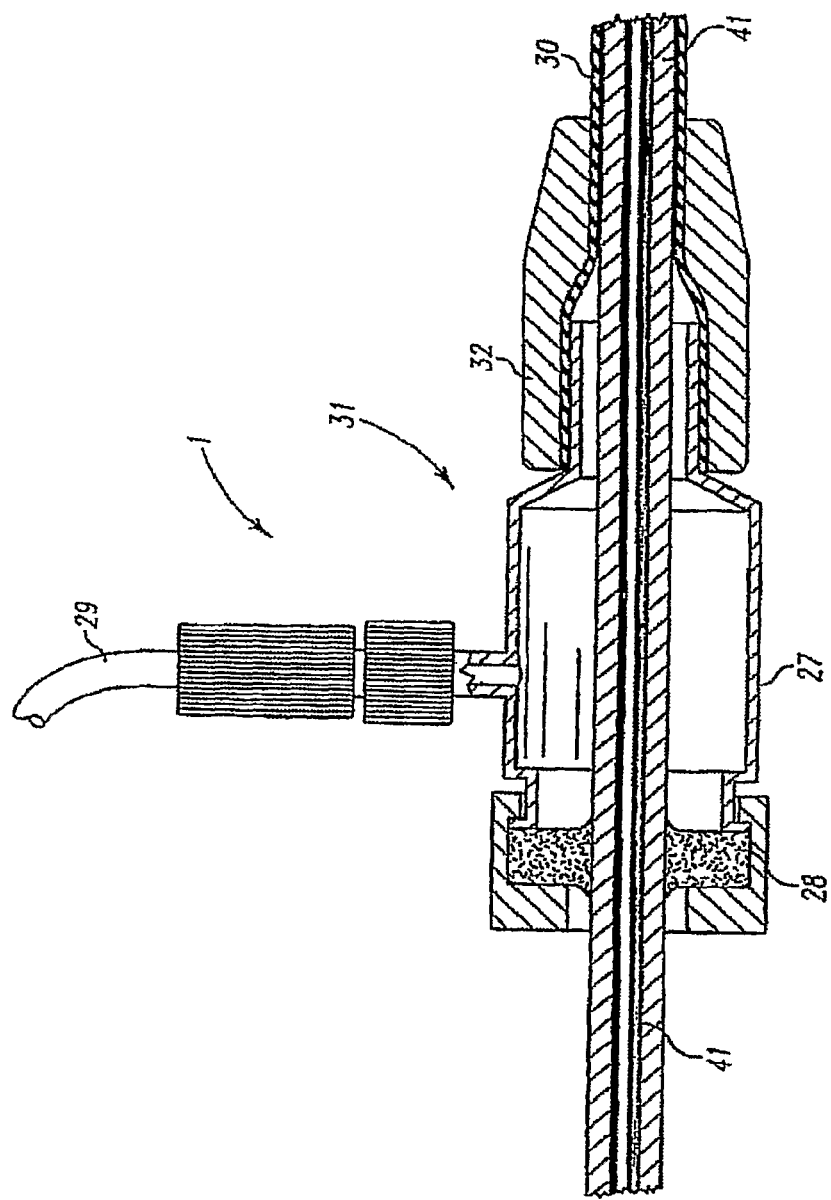
FIG. 5 is a sectional view of a portion of the introducer illustrating the haemostatic sealing means.

The tube 41 is "thick walled", which is to say the thickness of the wall of tube 41 is several times that of the thin walled tube 15. Preferably, the tube 41 is five or more times thicker than the thin walled tube 15. The sheath 30 is coaxial with and radially outside the thick walled tube 41. The thick walled tube 41 and the sheath 30 extend proximally to the manipulation region 1, as shown in FIG. 5. The thin walled tube 15 extends proximally to the proximal end of the introducer, as shown in FIG. 7. The introducer further includes haemostatic sealing means 31 radially disposed about the sheath and the thick walled tube 41. The haemostatic sealing means 31 control the loss of blood through the introducer during a procedure.

Figure 2A:
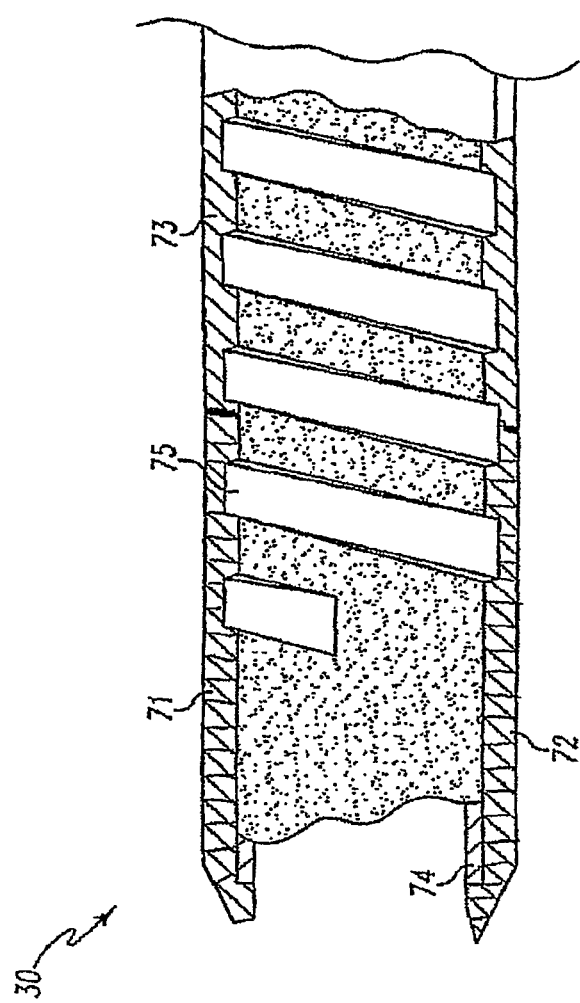
FIG. 2A is a sectional cutaway view of a portion of an introducer sheath.

FIG. 2A shows a sheath 30 according to an aspect of the present invention. The sheath 30 comprises an outer tube 71, an inner tube 74, and a flat wire coil 75. The inner tube 74 has a roughened outer surface. The flat wire coil 75 is compression fitted around the inner tube 74 within the outer tube 71. The inner tube 74 is made of polytetrafluoro-ethylene (PTFE) and is lubricious and slippery to facilitate insertion and withdrawal of the thick walled tube 41 and of catheters and the like therethrough. The outer tube 71 may be joined to the roughened outer surface of inner tube 74 between the spacings of the coil in accordance either with the disclosure of U.S. Pat. No. 5,380,304 or U.S. Published Patent Application No. 20010034514, both of which are incorporated by reference. The flat wire coil 75 provides the sheath 30 with superior kink-resistance.

The outer tube 71 may include a single tube section extending from the proximal to the distal end of the sheath 30. In this case, the outer tube 71 comprises, for example, nylon having a durometer of between about 50 D and 60 D (Shore D hardness). In certain applications, however it may be desirable for the tube section to have a hardness of up to 80 D.

Alternatively, in applications where it is desirable to have a highly flexible leading end of the sheath 30, for example where the sheath 30 must negotiate small, tortuous vessels, outer tube 71 may comprise multiple tube sections of varying hardness arranged axially with the sheath 30. For example, in FIG. 2A, outer tube 71 comprises a first tube section 72 located on a generally distal portion of the sheath 30 and a second tube section 73 located on a generally proximal portion of the sheath 30. The first and second tube sections 72, 73 are made of a suitable material, such as Nylon. The second tube section 73 can comprise, for example, nylon having a durometer of between about 50 D and 60 D, or as high as 80 D. The first tube section 72 comprises a generally lower durometer material than the second tube section 73. For example, the first tube section 72 may have a durometer of as low as about 10 D.

FIG. 2 illustrates a proximal prosthesis retention and release mechanism of the introducer. The proximal retention section 40 retains a proximal end 42 of the prosthesis 20 during the procedure. The proximal retention section 40 is coupled to the thick walled tube 41. Alternatively, the proximal retention section 40 may be formed in the thick walled tube 41. The proximal end 42 of the prosthesis 20 comprises an aperture defining a loop 43. A proximal trigger wire 44 extends through the loop 43 and through an aperture 45 in the distal attachment section 40 into the annular region between the thin walled tube 15 and the thick walled tube 41. The proximal trigger wire 44 extends proximally through the introducer from the proximal retention section 40 to the release wire actuation section located in the external manipulation section 1 (See FIG. 1). The trigger wire 44 couples the proximal end of the prosthesis 20 to the proximal retention section 40 during deployment. The prosthesis 20 can be selectively released into the body lumen by disengaging the trigger wire 44 from the loop 43.

Figure 4:
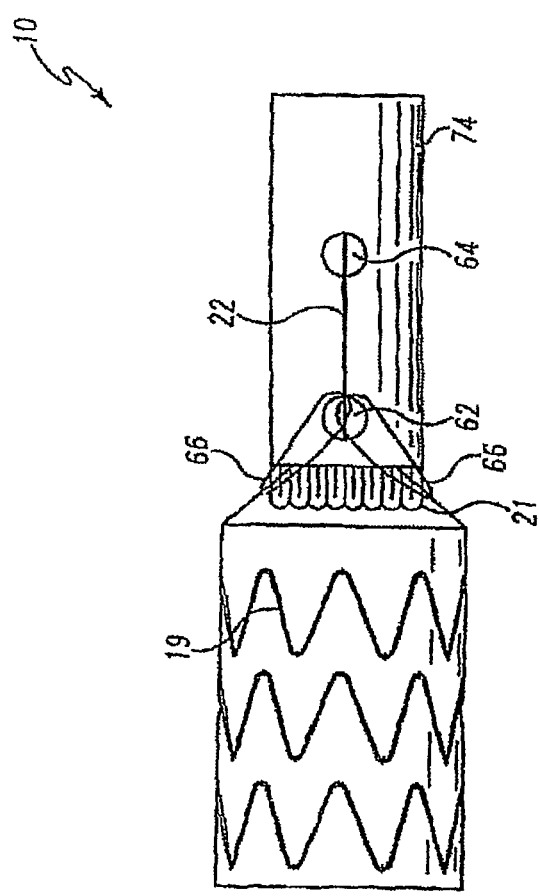
FIG. 4 is a sectional view of a distal retention device of the introducer.

FIGS. 3 and 4 illustrate a distal retention and release mechanism of the introducer. The distal attachment region 3 includes a retention device 10. The retention device 10 holds the distal end of the self-expanding zigzag stent 21 in a compressed state. The self-expanding zigzag stent 21 is retained in the retention device 10 by suture loops 66 and a distal trigger wire 22. The distal retention device 10 includes apertures 62 and 64 to accommodate the distal trigger wire 22. The suture loops 66 are coupled to the body of the prosthesis 20, and hold the self-expanding zigzag stent 21 in the retention device 10 until the trigger wire 22 is removed. While the trigger wire 22 is in place, the suture loops 66 prevent the retention device 10 and the prosthesis 20 from separating. The trigger wire 22 retains the suture loops 66 against an outer surface of the retention device 10. The distal trigger wire 22 extends proximally through the introducer from the distal retention device 10 to a release wire actuation section located in the manipulation section 1 (See FIG. 1).

As shown in FIG. 4, the suture loops 66 are attached to opposing sides of the prosthesis 20, for example separated by 90 to 180 degrees. The suture loops 66 are generally inelastic and do not stretch. Since the suture loops 66 do not stretch, they provide opposing torques that prevent the prosthesis 20 from rotating within the retention device 10. This configuration differs from introducers that have a single point of attachment. Such introducers may allow the stent to rotate within the retention device and lead to entanglement of the stent's struts. When the trigger wire 22 is removed, the suture loops 66 are free to move. The retention device 10 may then be released from the self-expanding zigzag stent 21 by sliding the retention device 10 distally away from the prosthesis 20.

The retention device 10 has at its distal end a long tapered flexible extension 11. The flexible extension 11 comprises an internal longitudinal aperture 12. The longitudinal aperture 12 facilitates advancement of the tapered flexible extension 11 along a previously inserted insertion wire 13. The longitudinal aperture 12 also provides a channel for the introduction of medical reagents. For example, it may be desirable to supply a contrast agent to allow angiography to be performed during placement and deployment phases of the medical procedure.

The distal end of the thin walled tube 15 is coupled to the flexible extension 11. The thin walled tube 15 is flexible so that the introducer can be advanced within a relatively tortuous vessel, such as a femoral artery. The thin walled tube extends proximally through the introducer to the manipulation section 1, terminating at a connection means 16, as shown in FIG. 7. The thin walled tube 15 is in mechanical communication with the flexible extension, allowing the operator to axially and rotationally manipulate the distal attachment region 3 with respect to the prosthesis 20. The connection means 16 is adapted to accept a syringe to facilitate the introduction of reagents into the thin walled tube 15. The thin walled tube 15 is in fluid communication with the aperture 12 of the flexible extension 11. Therefore, reagents introduced into connection means 16 may pass through aperture 12 and can emanate from lateral apertures 14 into the body lumen.

Figure 6:
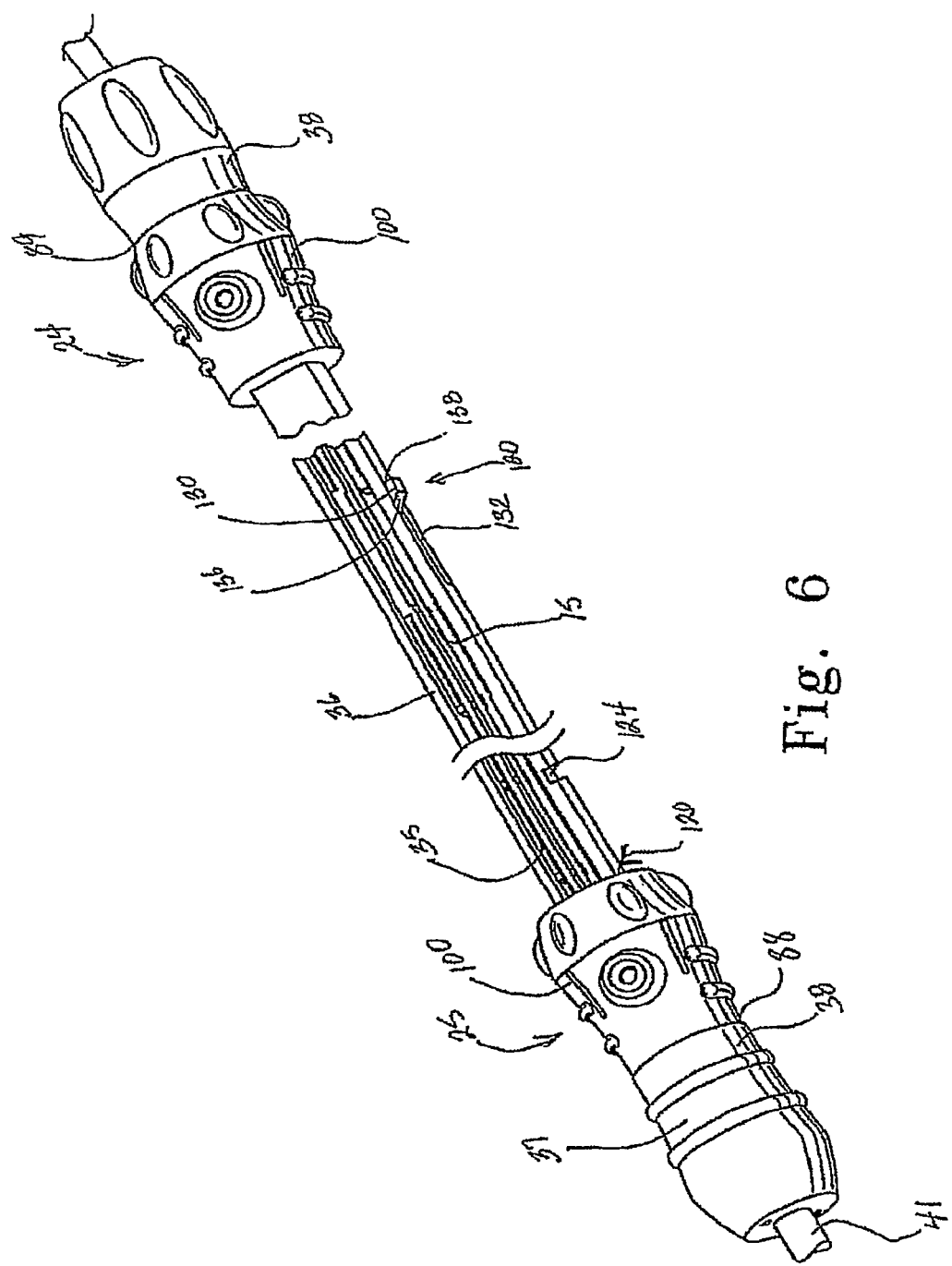
FIG. 6 is a perspective view of a trigger wire release mechanism of an introducer.

FIG. 6 shows the release wire actuation section of the external manipulation section 1. The release wire actuation section comprises an elongate body 36. Distal and proximal wire release mechanisms 24, 25 are disposed on the elongate body 36. End caps 38 are disposed on proximal and distal ends of the elongate body 36. End caps 38 comprise longitudinally-facing laterally opposed surfaces defining distal and proximal stops 88, 89. Distal and proximal wire release mechanisms 24, 25 are slidably disposed on the elongate body 36 between distal and proximal stops 88, 89. Distal and proximal stops 88, 89 retain the distal and proximal wire release mechanisms 24, 25 on the elongate body 36. The release wire actuation section comprises a locking mechanism 120 for limiting the axial displacement at wire release mechanisms 24, 25 on the elongate body 36.

The elongate body 36 is coupled to and extends longitudinally from the thick walled tube 41. The thin walled tube 15 passes through a chamber 35 formed longitudinally through the elongate body 36. Distal and proximal trigger wires 22, 44 (FIGS. 3 and 2, respectively) extend proximally from the annular space between the thick walled tube 41 and the thin walled tube 15 and into the chamber 35. The proximal end of the distal trigger wire 22 is coupled to distal wire release mechanism 24. The proximal end of the proximal trigger wire 44 is coupled to proximal wire release mechanism 25.

The suture loops 66, the trigger wire 22, and the distal wire release mechanism 24 form a control member to selectively release the retention device 10 from the prosthesis 20. The proximal trigger wire 44 and the proximal wire release mechanism 25 form a control member to selectively release the proximal retention section 40 from the prosthesis 20. To release the retention device 10 from the prosthesis, the distal control member is actuated by moving the distal wire release mechanism 24 from a distal end to a proximal end of the elongate body 36, thereby disengaging the distal trigger wire 22 from the retention device 10. The distal attachment region 3, including the retention device 10 can then be slid distally away from the prosthesis 20 allowing the self-expanding stent 21 to expand into the body lumen. To release the prosthesis 20 from the proximal retention section 40, the proximal control member is actuated by moving the proximal wire release mechanism 25 from a distal end to a proximal end of the elongate body 36, thereby disengaging the proximal trigger wire 44 from the prosthesis 20.

Figure 6A:
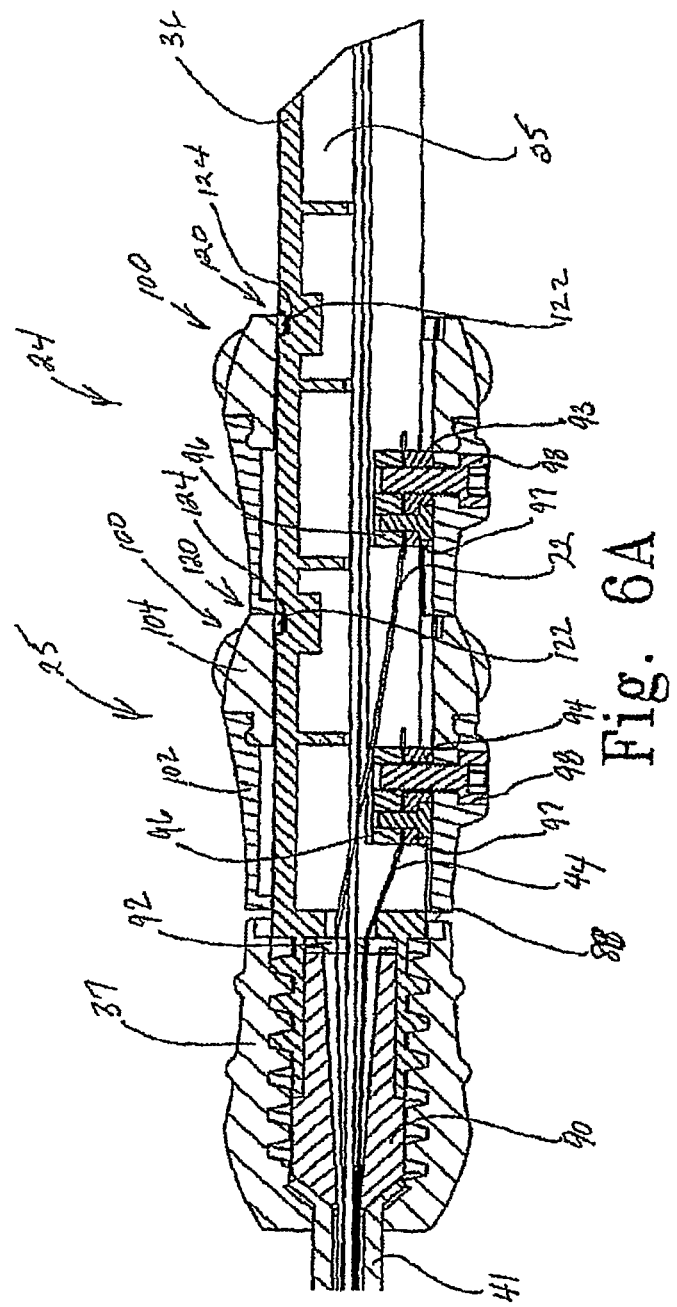
FIG. 6A is a sectional detail view of a trigger wire release mechanism of an introducer.

FIG. 6A shows a longitudinal cross-section view of the release wire actuation section in a pre-deployment state. Collar 37 couples thick walled tube 41 to the elongate body 36. Compression member 90 and gasket 92 are disposed between the thick walled tube 41 and the elongate body 36 to provide a seal. Gasket 92 may comprise silicone rubber. Distal trigger wire 22 is coupled to distal wire release mechanism 24 with a securing member 93. Similarly, proximal trigger wire 44 is coupled to proximal wire release mechanism 25 with a securing member 94. Securing members 93, 94 are adapted to fixedly secure the trigger wires 22, 44 to the respective wire release mechanism 24, 25. For example, securing members 93, 94 may comprise a pair of clamp blocks 96, 97 and a compression bolt 98 as shown in FIG. 6A, wherein the trigger wire is sandwiched between opposed faces of clamp blocks 96, 97 and secured therebetween by the compression bolt 98. Alternative designs for securing members 93, 94 are contemplated and may be utilized. Securing members 93, 94 form guide members for guiding trigger wires 22, 44 along the elongate body 36.

Distal and proximal wire release mechanisms 24, 25 may extend radially about the elongate body 36 to form a knob 100. Knob 100 may comprise a single unitary body. Alternatively, knob 100 may comprise multiple components. As shown in FIGS. 6 and 6A, knob 100 may comprise a body portion 102 and a head portion 104, wherein the head portion 104 is rotatably coupled to the body portion 102 about a longitudinal axis. FIG. 6B illustrates a perspective view of the distal end of head portion 104. The head portion 104 comprises a generally cylindrical body having an interior surface and an exterior surface. The distal end of head portion 104 includes an engaging structure 106 for rotatably coupling the head portion 104 to the body portion 102. The engaging structure 106 includes an annular flange 108 extending radially from the distal end of the head portion 104. The annular flange 108 is adapted to engage an annular retaining groove in an inner surface of the body portion proximal end 102 (not shown).

The head portion 104 may include a tactile member 110 on the exterior surface. Alternately, head portion 104 may include a plurality of tactile members 110 radially disposed about the exterior surface. Tactile members 110 may comprise a depression in the surface of the head portion 104. Alternately, tactile members 110 may comprise a projection on the surface of the head portion 104. Tactile members may comprise any shape or size so as to create a textured or non-uniform surface on the head portion 104, thereby giving the operator greater leverage to facilitate rotation of the head portion 104 with respect to the body portion 102.

The release wire actuation section may comprise a locking mechanism 120 for limiting the axial displacement of wire release mechanism 24, 25 on the elongate body 36. FIG. 6A illustrates a locking mechanism 120. The rotatable head portion 104 of the wire release mechanism 24, 25 is adapted to engage the elongate body 36. The locking mechanism 120 includes an engageable projection 122 disposed radially inward from the inner radial surface of the head portion 104. The locking mechanism 120 also includes a recessed portion 124 formed in an exterior surface of the elongate member 36 and adapted to receive the engageable projection 122. The head portion 104 can be rotated to selectively engage or disengage the engageable projection 122 within the recessed portion 124.

FIG. 6C illustrates a perspective view of the proximal end of the head portion 104 comprising a portion of a locking mechanism 120. The head portion 104 comprises a quarter-turn locking mechanism. The head portion 104 can be rotated ninety degrees in a first direction from a locked position into an unlocked position. Similarly, the head portion 104 can be rotated ninety degrees in a second direction, opposite the first direction from the unlocked position into the locked position. The locked position is indicated by orientation A in which the engageable projection 122 is aligned within the recessed portion 124 of the elongate body 36 (not shown). When the engageable projection 122 engages the recessed portion 124, the wire release mechanism 24, 25 is locked in place, thereby preventing actuation of the respective proximal or distal control member. The unlocked position is indicated by orientation B in which the recessed portion 104 of the elongate body is free of the engageable projection 122, thereby allowing actuation of the respective proximal or distal control member. In orientation B, the wire release mechanism 24, 25 is free to slide along the elongate body 36.

Alternative locking mechanisms within the scope of the present invention are contemplated. For example, the engageable projection may be disposed on the elongate body and the recessed portion may be disposed in the head portion 104.

FIG. 6 illustrates a locking mechanism 120 according to another aspect of the present invention. The locking mechanism is adapted to limit axial displacement of the wire release mechanisms 24, 25 on the elongate body 36. Locking mechanism 120 comprises a stay 130. Stay 130 extends radially through an aperture 132 formed in the elongate body 36. The stay 130 is coupled to the elongate body 36 through a biasing member 134. Biasing member 134 biases the stay 130 so that a portion of the stay 130 normally extends radially outward of the exterior surface of the elongate body 36.

Locking mechanism 120 allows wire release mechanisms 24, 25 to slide over the stay 130 in a first direction, but prevents wire release mechanisms 24, 25 from sliding over the stay 130 in a second, opposite direction. For example, the locking mechanism 120 of FIG. 6 is configured to allow wire release mechanism 24, 25 to slide from a distal end of the elongate body 36 over the stay 130 to a proximal end of the elongate body 36. However, the locking mechanism prevents the wire release mechanism 24, 25 from returning to the distal end of the elongate body 36 once the wire release mechanism 24, 25 has traversed the stay 130.

The stay 130 comprises a distal contact surface 136 and a proximal contact surface 138. The proximal contact surface 138 is generally normal to the surface of the elongate member 36 through which the stay 130 extends. The distal contact Surface 136 has an angle relative to the surface of the elongate member 36 through which the stay 130 extends such that when wire release mechanism 24, 25 contacts the stay from a distal end of the elongate member 36, the wire release mechanism 24, 25 exerts a radially inward force on the stay. The force acts on the biasing member, causing the stay 130 to retract into the aperture 132. The release mechanism 24, 25 may thereby traverse the stay 130. Conversely, when wire release mechanism 24, 25 contacts the stay from a proximal end of the elongate member 36, the wire release mechanism 24, 25 exerts only an axial force on the stay, preventing the stay 130 from retracting through the aperture 132 and the wire release mechanism 24, 25 from traversing the stay 130. Wire release mechanism 24, 25 is thereby prevented from returning to the distal end of the elongate body 36.

Prior to deployment of the prosthesis 20, the distal and proximal wire release mechanisms 24, 25 are positioned on a distal end of the body 36 as shown in FIG. 6A. The distal wire release mechanism 24 is in a generally proximal position with respect to the proximal wire release mechanism 25. The positioning of the distal and proximal wire release mechanisms 24 and 25 is such that the distal wire release mechanism 24 must be moved before the proximal wire release mechanism 25 can be moved. Therefore, the proximal end 42 of the prosthesis 20 cannot be released until the self-expanding zigzag stent 21 has been released and anchored to the lumen.

FIG. 5 shows the haemostatic sealing means 31 of the external manipulation section 1 in greater detail. The haemostatic sealing means 31 includes a haemostatic seal 27 and a clamping collar 32 that clamps the sheath 30 to the haemostatic seal 27. The haemostatic seal 27 may also include a seal ring 28 which may be made of silicone. The seal ring 28 forms a haemostatic seal around the thick walled tube 41. The haemostatic seal also includes a side tube 29 that facilitates the introduction of medical reagents between the thick walled tube 41 and the sheath 30.

Figure 5A:
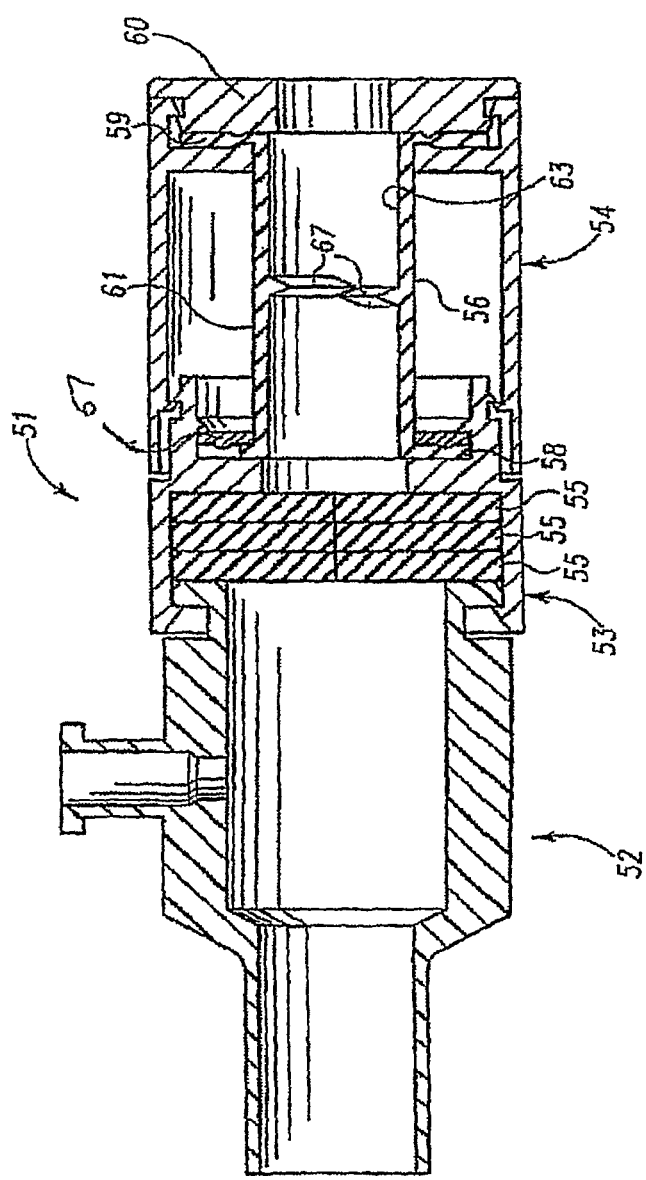
FIG. 5A is a sectional view of a haemostatic valve assembly.

The haemostatic sealing means 31 may comprise a haemostatic valve assembly 51 as shown in FIG. 5A. The haemostatic valve assembly 51 includes a cannula body 52, a base member 53 and a rotatable member 54. The cannula body 52 is positioned at a generally distal portion of the device and the rotatable member 54 is positioned at a generally proximal portion of the device. A check valve is disposed longitudinally between cannula body 52 and base member 53. In the embodiment shown, the check valve comprises one or more (three are shown in the embodiment) valve disks 55.

Valve disks 55 are preferably conventional check flow disks. Such valve disks are commercially available, and may be obtained, for example, from Cook, Inc., of Bloomington, Ind., under the name CHECK-FLO® valves. Valve disks 55 include a slit for passage of an interventional device (not shown) therethrough. Preferably, valve disks 55 have a slit on each face thereof. The slits may extend either partially or fully through the disk. Disks of this type are well known in the art. Three valve disks may be stacked and arranged such that the slits are aligned. However, those skilled in the art will appreciate that other numbers of disks may be utilized, and that the slits in the disks need not be aligned.

An elastomeric valve sheath 56 of the "iris"-type is disposed between base member 53 and rotatable member 54. The rotatable member 54 is rotatably coupled with respect to and around a common axis with the base member 53. Iris valves are known in the art and are described, for example, in the incorporated-by-reference U.S. Pat. No. 5,158,553. A washer 57 is provided to secure a distal flange 58 of the iris valve to the base member 53. An end cap 60 is provided at the proximal end of the device. The end cap 60 secures a proximal flange 59 of the iris valve to the rotatable member 54.

The elastomeric valve sheath 56 comprises a generally cylindrical body 61. The valve sheath 56 may include a ribbed structure that projects radially into the center of the valve sheath. The projecting ribbed structure is believed to enhance the seal formed by the valve sheath by inhibiting the possibility of gap formation when the iris valve is closed. The formation of the longitudinal gaps can be problematic with conventional iris seals, particularly when smaller diameter interventional devices are inserted therethrough.

The ribbed structure comprises one or more segments that extend circumferentially along part, or all, of the internal circumference of the valve member. Preferably, the ribbed structure is positioned substantially at or near the axial midpoint of the valve sheath. In the embodiment shown, the ribbed structure comprises a plurality of rib members 67. Rib members 67 are circumferentially spaced along inner valve surface 63, and are slightly axially offset from each other. In the embodiment illustrated, three rib members 67 are employed. Each of the rib members 67 spans about one-third of the inner circumference of the valve member, such that in combination as shown, the rib members substantially span the entire inner circumference of the valve member. The longitudinal ends of each of the rib members 67 preferably overlap slightly as the members are spaced along the circumference of the inner surface of the valve sheath. Preferably, the ribbed members have a generally triangular shape in cross-section, although other shapes may be substituted. When the iris valve is closed, the presence of the rib members 67 interact to comprise a lock (similar to that provided in well-known plastic locked bags) that is capable of providing a substantially gap-free seal. Further aspects of the haemostatic valve assembly 51 are provided in the incorporated-by-reference U.S. Published Patent Application No. 20050171479.

During a procedure, blood-loss may generally be controlled by the check valve by one or more valve disks 55. The check valve, however may not effectively control blood loss over a wide range of interventional device diameters (for example, 0.089 cm (0.035 in.) to 0.635 cm (0.250 in.)). Where the check valve is insufficient to control blood loss, the iris-type valve may be manually adjusted as a backup.

The iris-type valve may be adjusted between an open state and a constricted state by manually rotating the rotatable member 54 with respect to the base member 53. Because the distal flange 58 and the proximal flange 59 of the elastomeric valve sheath 56 are secured to the base member 53 and the rotatable member 54 respectively, rotation of the rotatable member 54 causes an axially intermediate portion (existing between the fixed distal and proximal flanges, 58, 59) of the valve sheath 56 to twist on itself from the open state to the constricted state. As the center opening of the valve is twisted, the valve constricts around the interventional device. Such constriction results in the formation of a haemostatic seal between the valve and the interventional device inserted therethrough.

Constriction of a center passageway of an iris valve in this manner is known in the art, and is further described and illustrated in the incorporated-by-reference U.S. Pat. No. 5,158,553 and the incorporated-by-reference U.S. Published Patent Application No. 20050171479.

FIG. 7 shows a proximal portion of the external manipulation section 1. A pin vise 39 is mounted onto the proximal end of the elongate body 36. The pin vise 39 has a screw cap 46. When screwed in, the vise jaws 47 clamp against (engage) the thin walled metal tube 15. When the vise jaws 47 are engaged, the thin walled tube 15 can only move with the body 36, and hence the thin walled tube 15 can only move with the thick walled tube 41 (not shown). With the screw cap 46 tightened, the entire assembly can be moved as one with respect to the sheath 30.

The introducer may include a prosthesis control member 81 as illustrated in FIG. 1. The prosthesis control member 81 is disposed on the dilator portion 34 of the external manipulation section 1. During deployment of the prosthesis 20, the sheath 30 is withdrawn proximally over the thick walled tube 41. The haemostatic sealing means 31 generally fits tightly about the sheath 30, resulting in a great amount of friction between the sheath 30 and the thick walled tube 41. As a result, withdrawal of the sheath 30 over the thick walled tube 41 can be difficult. In order to overcome the friction, the operator must have a very tight grip on the thick walled tube 41. Axial positioning of the prosthesis 20 may be compromised by the difficulty in gripping the thick walled tube 41.

The control member 81 solves this problem by providing the operator with a better grip on the dilator and by decreasing the force that the operator must exert to control and stabilize the thick walled tube 41 during sheath withdrawal. The control member 81 is generally tubular and comprises an inner dilator facing surface 82 and an outer grip surface 83. The control member 81 is slidably disposed on the thick walled tube 41 between the haemostatic sealing means 31 and the release wire actuation section. This allows the operator to slide the control member 81 (before gripping or squeezing it against dilator portion 34) so that it can be used at any position along the dilator.

The outer grip surface 83 is adapted so that the control member 81 fits the operator's hand comfortably and securely. As such, the outer grip surface 83 may have a diameter that greatly exceeds the diameter of the thick walled tube 41. The outer grip surface 83 may be generally axially uniform. Alternately, the outer grip surface 83 may be generally axially non-uniform, resulting in a contoured gripping surface. FIG. 1 illustrates a control member 81 having a generally non-uniform outer grip surface 83, wherein the control member is generally shaped like an hour glass.

The outer grip surface 83 may comprise a smooth surface finish, or alternately, the outer grip surface may comprise a rough or textured surface finish. Rough or textured surface finishes are beneficial because they provide increased surface area contact between the operator and the control member 81, thereby increasing the operator's leverage. Multiple surface finishes may be selected to provide various utilitarian and tactile benefits.

The control member 81 is generally deformable so that when the operator grips the control member 81, the control member 81 compresses against the thick walled tube 41. The control member 81 transfers the force exerted by the operator to the thick walled tube 41. The dilator facing surface 82 may comprise a generally smooth surface. Alternatively, the dilator facing surface 82 may have a rough or textured surface. A rough or textured surface may create a more "sticky" or "tacky" contact between the control member 81 and the thick walled tube 41, thereby increasing the force that is transferred by the operator to the dilator.

The dilator facing surface 82 may comprise a generally uniform surface. Alternately, the dilator facing surface 82 may comprise a generally non-uniform surface. For example, the dilator gripping surface 82 may comprise a plurality of engageable projections that extend radially inward towards the thick walled tube 41. When the operator grips the control member 81 against the thick walled tube 41, engageable projections engage the surface of the thick walled tube. Engageable projections increase the surface contact area between the control member 81 and the thick walled tube, thereby increasing the force that the control member transfers from the operator to the thick walled tube 41.

Engageable projections may comprise any geometric or non-geometric shape. For example, engageable projections may include "O" shapes, lines, dashes, "V" shapes, or the like.

Gripping member 81 comprises a soft, deformable, or generally low durometer material. The gripping member 81 may comprise a material with generally tacky surface properties. Accordingly, the gripping member 81 may be made of silicone rubber. Alternatively, in accordance with the present invention, the gripping member may be made of any suitable natural, thermoplastic, or thermoset material known in the art.

The various stages of deployment of the prosthesis 20 will now be explained. A guide wire 13 is introduced, for example, into the femoral artery and advanced until the tip of the guide wire 13 is beyond the region into which the prosthesis 20 is to be deployed. The introducer assembly is then inserted through the femoral artery over the guide wire 13, and positioned by radiographic techniques, generally known in the art. At this stage, the ends of the prosthesis 20 are retained by the distal and proximal retaining assemblies respectively and the sheath 30 is disposed over and covers the length of the prosthesis 20.

Once the introducer assembly is in a desired position for deployment of the prosthesis 20, the operator withdraws the external sheath 30 in a proximal direction from its original position to a position just distal of the proximal attachment section 40. The operator pulls the haemostatic valve assembly 51, and consequently the sheath 30 in a proximal direction while holding the dilator portion 34 steady. To hold the dilator portion steady, and thereby control the position of the prosthesis 20, the surgeon may grasp the control member 81. The control member 81 may be slidably positioned at any position along the dilator portion 34 according to the operator's requirements.

By withdrawing the external sheath 30, the surgeon releases the middle portion of the prosthesis 20 so that the middle portion can expand radially. The distal self-expanding stent 21, however, is still retained within the retention device 10 as shown in FIG. 3. Also, the proximal end 42 of the prosthesis 20 is still retained within the sheath 30 as shown in FIG. 2.

Next, the operator may release the pin vise 39, shown in FIG. 7, to allow movement of the thin walled tube 15 with respect to the thick walled tube 41. The operator may make small movements of the thin walled tube to lengthen, shorten, rotate, or compress the prosthesis 20 for accurate placement in the desired location within the lumen. X-ray opaque markers (not shown) may be placed along the prosthesis 20 to assist with placement of the prosthesis.

When the prosthesis 20 has been properly located in the body lumen, the distal trigger wife 22 is disengaged so that the retention device 10 can separate from the self-expanding zigzag stent 21. First, the distal trigger wire release mechanism 24 is disengaged from the elongate body 36 by actuating the locking mechanism 120, shown in FIG. 6A. The operator turns the head portion 104 of the knob 100 to release the engageable projection 122 from the recessed portion 124 of the elongate body 36, allowing the release mechanism 24 to move freely along the elongate body 36. The operator then slides the knob 100 proximally to a proximal end of the elongate body 36. The proximal stop 89 retains the release mechanism 24 on the elongate body 36. The knob 100 moves the distal wire guide proximally in the chamber 35, causing the trigger wire 22 to disengage from the retention device 10 (shown in FIG. 3). The knob 120 traverses the stay 130. Once the distal trigger wire release mechanism 24 is slid to the proximal end of the body 36, as shown in FIG. 6, the locking mechanism 120 prevents the distal trigger wire release mechanism 24 from returning to its original position.

Next, the screw cap 46 of the pin vise 39 (shown in FIG. 7) is loosened so that the thin walled tube 15 can be pushed in a distal direction, thereby moving the retention device 10 in a distal direction. When the distal attachment means 10 no longer surrounds the self-expanding stent 21 at the distal end of the prosthesis 20, the self-expanding stent 21 can expand. When the self-expanding stent 21 expands, the hooks or barbs 26 on the self-expanding stent 21 grip onto the walls of the lumen to hold the distal end of the prosthesis 20 in place.

At this point, the proximal end 42 of the prosthesis 20 is still retained by the proximal retention section 40. The proximal trigger wire 44 extends through the loop 43, retaining the prosthesis 20 to the delivery system, as shown in FIG. 2. The external sheath 30 is withdrawn to proximal of the proximal attachment section 40 to allow the proximal end 42 of the prosthesis 20 to expand. At this point, the proximal end 42 of the prosthesis 20 is not anchored in the body lumen and may still be moved. Consequently, the prosthesis 20 can be rotated or lengthened or shortened or otherwise moved for accurate positioning. Where the prosthesis 20 to be deployed is a bifurcated graft, the movement at this stage may ensure that the shorter leg is directed in the direction of the contra-iliac artery.

Next, the proximal end 42 of the prosthesis 20 is released by disengaging the proximal trigger wire 44. First, the proximal trigger wire release mechanism 25 (shown in FIG. 6A) is disengaged from the elongate body 36 by actuating the locking mechanism 120 as described above with respect to the distal wire release mechanism 24. Once the release mechanism 25 is unlocked from the elongate body 36, the operator slides the knob 100, proximally from its initial position at the distal end of the elongate body 36 (shown in FIG. 6) to a proximal end of the body 36. The knob 100 moves the proximal wire guide proximally in the chamber 35, causing the trigger wire 44 to disengage from the prosthesis 20. The knob 100 traverses the stay 130. Once the proximal trigger wire release mechanism 25 is slid to the proximal end of the body 36, the locking mechanism 120 prevents the release mechanism 25 from returning to its original position. At this point, the proximal trigger wire release mechanism 25 is situated adjacent the distal trigger wire release mechanism 24. The loop 43 of the terminal distal self-expanding zigzag stent 19 is hence released, and the prosthesis 20 is free and expands to the walls of the vessel.

At this point, the introducer is ready to be removed. To remove the introducer, the proximal attachment section 40 is advanced until it is received in the rear of the distal attachment device 10. The distal attachment device 10, the tapered flexible extension 11, the proximal attachment device 40, and the sheath may then be removed together. Alternatively, the sheath can be removed at a later time than the other items.

An advantage of the release wire mechanisms of the above-described embodiments is that the release of each of the prosthesis retaining devices is relatively convenient quick and simple. This contrasts with prior art arrangements comprising removable rings with set screws in which a relatively long and complicated procedure is necessary to remove the set screw, to pull and remove the ring and then to pull the entire release wire from the introducer. An advantage of the flexible sheath 30 is that it can maintain a round, smooth shape even in areas where it constricts or holds the stent graft in the tightly packed, folded configuration. This allows a smoother, easier retraction of the sheath from off the prosthesis at deployment.

In addition, the sheath 30 is kink resistant due to its coil reinforcement in the wall. Large diameter, thin walled sheaths are prone to kinking when exposed to bending forces when a small or no device is in the lumen of the sheath. A kinked sheath is un-useable and must be replaced. The sheath 30 substantially eliminates the chance for sheath kinking while remaining flexible enough to negotiate tortuous anatomy and the aortic arch. Flexibility and the ability to contain a folded or collapsed stent graft or other prosthesis are opposing constraints. The usual PTFE sheath material is a compromise for both requirements. The construction of sheath 30 has increased flexibility with increased resistance to kinking and diametrical deformation (ability to maintain a round shape and a smooth lumen). An advantage of the different types of control elements for the various mechanisms of the introducer device makes it possible to an operator to manipulate the delivery system without having to look directly at the various parts of the device. Each component has a feel that communicates to the operator what it is and what motions it requires. This is important to the operator because he or she normally watches the progress of the stent graft placement and deployment on a fluoroscope which is above the patient usually at the operator's eye level. Not having to look back and forth between the fluoroscope and the delivery system allows the operator to concentrate without interruption on the actual placement and deployment of the stent graft. This is important because it is critical that the stent graft be placed as close to the renal arteries as possible without having any portion of the stent graft across the origin of the renal arteries. Restricted or loss of blood flow to the kidneys would result. Any instantaneous lack of attention or interruption in the deployment process could result in slight movement of the stent graft at the moment of deployment. An advantage of including valve 56 in addition to valve assembly 51 is to control any blood seepage around assembly 51. The extra valve also provides safety redundancy in that if one valve fails, the other valve can control bleeding to a safe amount. Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. For example the prosthesis 20 may not be self-expanding; it could be a balloon-expandable prosthesis, although this would require a more complicated introducer arrangement. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A trigger wire release mechanism for releasing a retained end of a prosthesis, the trigger wire release mechanism comprising:
   a prosthesis retaining device arranged to engage an end of the prosthesis;
   a trigger wire having a distal end and a proximal end, the distal end being arranged to selectively couple the prosthesis retaining device to the prosthesis;
   a control mechanism comprising an elongate body member and a guide member including a securing member, the elongate body member having a proximal end and a distal end, an exterior surface, and an interior surface, the interior surface defining a chamber extending longitudinally with the elongate body member, wherein the securing member is disposed within the chamber;
   wherein the trigger wire proximal end is operably coupled to the securing member in the chamber and the guide member is slidably disposed between a generally distal position and a generally proximal position along the elongate body member and the securing member is slidably disposed between a generally distal position and a generally proximal position within the chamber and with the guide member to selectively disengage the distal end of the trigger wire from the prosthesis retaining device and to selectively disengage the prosthesis retaining device from the prosthesis.

2. The trigger wire release mechanism of claim 1 wherein the control mechanism further comprises a locking mechanism to limit axial movement of the guide member along the elongate body.

3. The trigger wire release mechanism of claim 2 wherein the locking mechanism allows the guide member to move from the distal end of the elongate body member to the proximal end of the elongate body member.

4. The trigger wire release mechanism of claim 3 wherein the locking mechanism prevents the guide member from moving from the proximal end of the elongate body member to the distal end of the elongate body member.

5. The trigger wire release mechanism of claim 2, wherein the locking mechanism comprises a stay that extends through an aperture formed in the elongate body member, the stay being coupled to the elongate body member by a biasing member that biases the stay so that a portion of the stay extends radially outwardly from the exterior surface of the elongate body member to limit the axial movement of the guide member, wherein radial compression of the biasing member causes the stay to retract through the aperture allowing the guide member to traverse the stay.

6. The trigger wire release mechanism of claim 2, wherein the locking mechanism releasably fixes the guide member to the elongate body member.

7. The trigger wire release mechanism of claim 2, wherein the locking mechanism comprises an engageable member on one of the wire guide and the elongate body member and a receiving member on the other of the elongate body member and the wire guide, the receiving member adapted to selectively receive the engageable member to fix the guide member to the elongate body member.

8. The trigger wire release mechanism of claim 1 wherein the guide member comprises a knob radially disposed about the elongate body member.

9. The trigger wire release mechanism of claim 8 wherein the knob comprises a body portion and a head portion, the trigger wire release mechanism further comprising a locking mechanism having an engageable member disposed on one of the head portion and the elongate body member and a receiving member disposed on the other of the elongate body member and the head portion, the head portion rotatably coupled to the body portion about a longitudinal axis of the elongate body member, wherein rotation of the head portion about the elongate body member selectively engages the engageable member and the receiving member, thereby preventing the knob from sliding along the elongate body member.

10. The trigger wire release mechanism of claim 1 wherein the control mechanism comprises a stop disposed on the proximal end of the elongate body member for retaining the guide member on the elongate body member.

11. The trigger wire release mechanism of claim 1 wherein the control mechanism further comprises a locking mechanism releasably fixing the guide member to the elongate body member and comprising an engageable member on one of the wire guide and the elongate body member and a receiving member on the other of the elongate body member and the wire guide, the receiving member adapted to selectively receive the engageable member to axially fix the guide member to the elongate body member.

12. The trigger wire release mechanism of claim 1 comprising first and second trigger wires attached to respective first and second prosthesis retaining devices located at opposite ends of the prosthesis.

13. An introducer for a prosthesis, the introducer comprising a trigger wire release mechanism according to claim 1.

14. The trigger wire release mechanism of claim 1, further comprising any two or more of the following:
   the control mechanism further comprises a locking mechanism to limit axial movement of the guide member along the elongate body member;
   the locking mechanism allows the guide member to move from the distal end of the elongate body member to the proximal end of the elongate body member;
   the locking mechanism prevents the guide member from moving from the proximal end of the elongate body member to the distal end of the elongate body member;
   the locking mechanism comprises a stay that extends through an aperture formed in the elongate body member, the stay being coupled to the elongate body member by a biasing member that biases the stay so that a portion of the stay extends radially outwardly from the exterior surface of the elongate body member to limit the axial movement of the guide member, wherein radial compression of the biasing member causes the stay to retract through the aperture allowing the guide member to traverse the stay;
   the locking mechanism releasably fixes the guide member to the elongate body member;
   the locking mechanism comprises an engageable member on one of the wire guide and the elongate body member and a receiving member on the other of the elongate body member and the wire guide, the receiving member adapted to selectively receive the engageable member to fix the guide member to the elongate body member;
   the guide member comprises a knob radially disposed about the elongate body member;
   the knob comprises a body portion and a head portion, the trigger wire release mechanism further comprising a locking mechanism having an engageable member disposed on one of the head portion and the elongate body member and a receiving member disposed on the other of the elongate body member and the head portion, the head portion rotatably coupled to the body portion about a longitudinal axis of the elongate body member, wherein rotation of the head portion about the elongate body member selectively engages the engageable member and the receiving member, thereby preventing the knob from sliding along the elongate body member;
   the control mechanism comprises a stop disposed on the proximal end of the elongate body member for retaining the guide member on the elongate body member;
   the control mechanism further comprises a locking mechanism releasably fixing the guide member to the elongate body member and comprising an engageable member on one of the wire guide and the elongate body member and a receiving member on the other of the elongate body member and the wire guide, the receiving member adapted to selectively receive the engageable member to axially fix the guide member to the elongate body member; and
   first and second trigger wires attached to respective first and second prosthesis retaining devices located at opposite ends of the prosthesis.

* * * * *

UNITED STATES PATENT AND TRADEMARK OFFICE
CERTIFICATE OF CORRECTION

PATENT NO. : 8,709,060 B2  Page 1 of 1
APPLICATION NO. : 12/158400
DATED : April 29, 2014
INVENTOR(S) : Thomas A. Osborne It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1434 days.

Signed and Sealed this

Twenty-ninth Day of September, 2015

Michelle K. Lee
*Director of the United States Patent and Trademark Office*